United States Patent [19]

Saint-Leger et al.

[11] Patent Number: 4,931,467
[45] Date of Patent: Jun. 5, 1990

[54] DRUG COMPOSITION FOR TREATING OR PREVENTING ACNE BY ORAL ADMINISTRATION

[75] Inventors: Didier Saint-Leger; Arlette Bague, both of Paris, France

[73] Assignee: L'Oreal, Paris, France

[21] Appl. No.: 758,646

[22] PCT Filed: Jan. 24, 1985

[86] PCT No.: PCT/FR85/00011
§ 371 Date: Jul. 11, 1985
§ 102(e) Date: Jul. 11, 1985

[87] PCT Pub. No.: WO85/03226
PCT Pub. Date: Aug. 1, 1985

[30] Foreign Application Priority Data

Jan. 25, 1984 [FR] France ............................ 84 01131

[51] Int. Cl.$^5$ ................... A61K 31/07; A61K 31/215
[52] U.S. Cl. ................... 514/529; 514/691; 514/703; 514/725; 514/859
[58] Field of Search ............ 514/725, 766, 529, 691, 514/703, 859

[56] References Cited

PUBLICATIONS

Chemical Abstracts 67: 72388p (Fegeler et al.), 1967.
Merck Index, 9th ed; 1926, pp. 1852–1855.

*Primary Examiner*—Leonard Schenkman
*Attorney, Agent, or Firm*—Cushman, Darby & Cushman

[57] ABSTRACT

This composition contains, by way of main active principle, in a pharmaceutically acceptable carrier, at least one substance belonging to the carotenoid family and chosen, in particular, from the group consisting of $\alpha$-carotene, $\delta$-carotene, $\gamma$-carotene, $\beta$, $\beta$-carotene-4,4'-dione, ethyl 8'-apo-$\beta$-caroten-8'-oate, $\beta$-apo-8'-carotenal, $\psi,\psi$-carotene, $\psi,\psi$-carotene-16,16'-diol and $\psi,\psi$-caroten-16-ol. This composition preferably contains from 0.001 to 10% by weight of active principle relative to the total weight of the composition and takes the form of a suspension, tablets or gelatin capsules. The pharmacological activity of this drug is an activity which inhibits comedo formation, the latter being due to an irritation caused by an excess of lipid oxide (oxidized squalene).

6 Claims, No Drawings

DRUG COMPOSITION FOR TREATING OR PREVENTING ACNE BY ORAL ADMINISTRATION

The present invention relates to a drug composition for treating or preventing acne by oral administration.

Until relatively recently, no large differences had been noted in the qualitative composition of the surface cutaneous lipids secreted by the skin of acne patients and individuals not suffering from acne.

By using thin layer chromatography, it has been possible to study the presence of lipid oxides in the cutaneous lipid secretions supplied by the sebaceous glands and inside an open or closed comedo. Thus, in an instance of thin layer chromatography of the surface cutaneous lipids, elution gave a succession of spots corresponding, respectively, to a polymerized and oxidized squalene, cholesterol, fatty acids, triglycerides, two other different oxidation states of squalene, waxes and unoxidized squalene, the latter being present in the secretion in the proportion of 10 to 15% by weight. The three substances which correspond to oxidized squalene are three different substances; that eluted in the first place has undergone, relative to squalene, a polymerization as a result of the presence of oxygen: this oxidized squalene is a very polar gum-polymer having an oxygen content of 25 to 28% by weight.

There have been carried out statistical measurements which have made it possible to verify that there is a strong correlation between the extent to which a skin is affected by acne and the presence of oxidized lipids of sebaceous and/or epidermal origin, and oxidized squalene in particular, in the layers of the said skin. This observation already appeared in a publication "Free Communications 289, FC 16-4 D, Article No. 386, Ayako Yamamoto", which reported the 16th Dermatological Congress in May 1982, and stated as a conclusion that normal human skin appeared to possess a factor which plays a role in the inhibition of the permeation of lipid oxides inside the epidermis, and that irritation of the skin and cytotoxicity by squalene oxides take place not only according to the level of lipid oxides but also depending on the chemical structure thereof. Furthermore, the studies of K. MOTOYOSHI, reported in the journal "British Journal of Dermatology", (1983) 109, 191–198, have demonstrated that the presence of oxidized lipids, and squalene oxides in particular, in the follicular infundibulum is highly comedogenic.

Thus, oxidized lipids, which prove to be cytotoxic and comedogenic for cutaneous tissue, can be considered to be largely responsible for the pathogenesis of acne. Moreover, it is known from the studies of O. H. MILLS, M. PORTE and A. M. KLIGMAN, "British Journal of Dermatology" (1978) 98, 145, that UV-A radiation increases the capacity of human sebum and squalene to produce comedos; it has hence been suggested that this radiation could increase the levels of lipid oxides, these oxides irritating the epithelium in the follicular infundibulum and hence increasing the formation of comedos.

In parallel with the studies thus performed by the specialists in basic research in the therapeutic field, specialist beauticians have, for their part, carried out experiments which have led to the following observations:

comedos appear to result from irritation caused by certain agents such as squalene oxides: thus, it has been possible to note the formation of comedos on a rabbit's ear which has received squalene oxide by topical application.

carotenoids are natural agents used in the cosmetics field for protecting the cutaneous tissue against peroxidation phenomena and photosensitisation phenomena and, as a general rule, phenomena of irritation by chemical means or by irradiation. Thus, apart from their function of coloring the skin for the purpose of tanning, illustrated in particular by French Patent No. 2,384,500, which describes a formulation for gelatin capsules based on β-carotene, and by French Patent No. 2,430,765, which describes a product consisting of pure carotene in a carrier, carotenoids are known, as a general rule, for their function of protecting against sunburn. Thus, French Patent Application No. 2,392,673 describes a formulation for gelatin capsules, the function of which is to color the skin, accelerate melanogenesis and protect from sunburn; this formulation contains β,β-carotene-4,4'-dione (canthaxanthin) and/or β-carotene. There is also known, from British Patent No. 1,375,436, a process for preparing a cosmetic composition, according to which process a large proportion of a vegetable oil is brought into contact with a small proportion of a source of vitamin K and β-carotene for sufficient time for the oil to have extracted part of the vitamin K and β-carotene; the product obtained can be used in topical applications for the purpose of protecting the skin against sunstroke. All these documents are only concerned with cosmetic applications linked to tanning of the skin and its protection against sunstroke.

Based on the observations described above, which, it should be noted, have been made by specialists in two different technical fields, namely dermatologists and beauticians, it was then put forward the hypothesis that carotenoids might protect cutaneous tissue against any attack of an irritant nature and, inter alia, would prevent the formation of comedos. It was not obvious that this hypothesis would be verified since it was known that comedos in acne are caused by an irritation due to squalene oxides, whereas carotenoids are known for their protective action in the case of irritation by irradiation, that is to say irritation of a different nature from that caused by squalene oxides. Surprisingly, it proved to be the case that carotenoids, administered orally, excluding β-carotene for the reason explained below, gave exceptionally good results for treating and preventing acne in all its forms, in particular acne vulgaris, nodulocystic acne and acne rosacea.

In the prior state of the art, mention was never made of this property intrinsically possessed by carotenoids.

Thus, Dutch Patent No. 87,724 describes the use of vitamin A or provitamin A, that is to say β-carotene, by way of active substance in the treatment, externally, of acne vulgaris. Moreover, this (pro)vitamin A is used in combination with a polyphenol, such as resorcinol, which constitutes another necessary active substance in the treatment of this disease.

Moreover, it emerges from the text of this Dutch patent that the provitamin A is only used inasmuch as it is capable of generating vitamin A.

According to the present invention, carotenoids which generate vitamin A, such as α-carotene and β-carotene, are active as such, in the same way as carotenoids which do not generate vitamin A such as δ-carotene, and not as substances capable of providing vitamin A. Polyphenols, which are never present in the compositions according to the invention, would in any case be of no use therein because, in contrast to vitamin A—which is also known as an ingredient in compositions for treating acne, from this Dutch patent and from other documents such as "MODERNE ARZNEIMITTEL", 5th Edition, 1980, page 1086, Schwarzhaupt drug Aknin ®—, carotenoids do not give rise to deleterious side effects such as hyper vitaminosis A.

This difference in behavior proves that carotenoids which generate vitamin A do not act, according to the present invention, by way of the vitamin A which they can yield under certain conditions. As further evidence for the truth of this, in a test on the oxidation of squalene which was performed by the present inventors, carotenoids which do not generate vitamin A behave in the same manner as those which generate vitamin A; it was observed that all the carotenoids tested in this way inhibited in the same manner, except in a few respects, the oxidation of squalene. Now, it is believed that oxidized squalene is responsible for acne. It should also be noted that vitamin A has no activity in this test, which shows still more clearly the lack of relationship between the behavior of the carotenoids of the present invention and the (pro)vitamin A of the abovementioned Dutch patent.

It is known, moreover, that, when ingested by the organism, carotenoids which generate vitamin A are stored in the liver, where they regenerate vitamin A according to the requirements, in a greater or lesser amount depending on the carotenoid used. Now, $\beta$-carotene will become converted to vitamin A to the greatest extent, and for this reason it is excluded from the family of carotenoids which constitute the active principle of the drug according to the present invention. A significant fraction of the other carotenoids which generate vitamin A occur in the cutaneous layers; as regards carotenoids which do not generate vitamin A, such as $\delta$-carotene or canthaxanthin, they occur entirely in the cutaneous layers.

The present invention hence has the aim of describing a therapeutic use of carotenoids, the toxic effect of which in man is zero; the invention relates to both the preventive aspect of the acne condition and the curative aspect thereof.

The present invention has as its subject the new drug constituted by a composition for treating or preventing acne by the oral route, this composition being characterised in that it contains, by way of main active principle, in a pharmaceutically acceptable carrier, at least one substance belonging to the carotenoid family, with the exception of $\beta$-carotene.

According to the invention, the main active principle of the composition for the treatment of acne is selected, in particular, from the group consisting of $\alpha$-carotene, $\delta$-carotene, $\gamma$-carotene, $\beta$-carotene-4,4'-dione (canthaxanthin), ethyl 8'-apo-$\beta$-caroten-8'-oate, $\beta$-apo-8'-carotenal, $\psi,\psi$-carotene (lycopene), $\psi,\psi$-carotene-16,16'-diol and $\psi,\psi$-caroten-16-ol (lycoxanthin).

The pharmacological activity possessed by carotenoids is an activity which is inhibitory in the formation of comedos associated with acne. This activity was demonstrated by experiments in vivo, the procedure for which, in accordance with the publication of Kligman A. M. and Kwong T., "British Journal of Dermatology" (1979) Volume 100, page 99, is given below.

These experiments are performed on a series of 5 male Bouscat rabbits weighing approximately 2.5 kg each. Throughout the experiments, the rabbits receive food and drink ad libitum.

Every morning, for 5 days out of 7, there is applied to one of the ears of each rabbit 0.1 ml of a suspension of $\beta$-carotene in propylene glycol, this suspension being formulated in the proportion of 1 mg of $\beta$-carotene for 1 ml of propylene glycol. This treatment is stopped after a total of 10 applications has been carried out on each rabbit.

Every afternoon on the days when the 5 rabbits have undergoing the above treatment, there is applied on both ears of each of these rabbits 0.1 ml of squalene oxide per ear.

The 5 rabbits are then sacrificed and the epidermis is separated from the dermis of each ear. The epidermis thereby removed is examined with the aid of a stereomicroscope. The comedos are assessed according to their size, using a visual scale ranging from 0 to 3, a value of 0 corresponding to an absence of comedo formation and a value of 3 to a maximum development of the latter. The results obtained as as follows:

the five ears pretreated with $\beta$-carotene contain comedos having an average size assessed at 1.2 on the abovementioned scale; as regards the five ears which have not been pretreated, these contain comedos the size of which has been able to be assessed at 1.8 on average.

This test of comedogenesis, using $\beta$-carotene in topical application, it being known that, by this route, it constitutes a very effective drug for treating acne, and for this reason constitutes an equivalent of the carotenoids of the present invention applied orally, illustrates the preventive action of carotenoids, and it is important to emphasise that vitamin A, which was proposed for treating acne, had never been put forward in preventive therapy. The present invention hence brings about substantial progress relative to the prior state of the art, which indicated drugs which could treat the acne condition only when it has declared itself, and even then with deleterious side effects.

The therapeutic compositions according to the present invention generally contain from 0.001 to 10% by weight of main active principle relative to the total weight of the composition.

Furthermore, the therapeutic compositions according to the present invention can also contain at least one known substance which is active in the treatment of acne and different from that or those belonging to the carotenoid family. They contain, for example, from 0.001 to 15% by weight of this other active substance relative to the total weight of the composition.

In addition, it is useful to prevent the oxidation of the carotenoids according to the invention.

To this end, according to a special characteristic of the present invention, the drug composition contains at least one antioxidant, in the proportion of 0.001 to 2% by weight relative to the total weight of the composition. The antioxidant or antioxidants is (or are) chosen, in particular, from vitamin E, t-butylhydroquinone, butylated hydroxyanisole and butylated hydroxytoluene.

The pharmaceutically acceptable carrier can contain, for example, water, gelatin, lactose, starch, talc, vaseline, gum arabic, polyalkylene glycols and magnesium stearate. The tablets, powders, granules, lozenges or gelatin capsules can contain binders, fillers, pulverulent carriers; the solutions or suspensions can contain diluents, solvents and thickeners.

In addition, there can be added at least one common adjuvant selected from the group formed by preservatives, palatability agents and colorings.

The pharmacological and galenical conversions of the compounds according to the invention are performed in a known manner. Carotenoids possess strictly no toxicity, with the result that there is theoretically no upper limit for administration thereof.

Carotenoids can be used, as described above, either in preventive therapy or in curative therapy. By virtue of their low toxicity and gentle action, their use can also be recommended in alternation with drugs for treating acne which, by virtue of their toxicity and very powerful action, require medical supervision and must of necessity be administered over limited periods of time.

In preventive therapy, carotenoids are not administered in combination with other substances which are active in treating acne. On the other hand, in curative therapy, carotenoids are used either alone or in combination with other active substances, in particular substances which are active in treating acne. In this latter case, the patient is administered either a single formulation containing simultaneously the desired carotenoid or carotenoids and at least one other active substance, or two different formulations, one containing the carotenoid or carotenoids and the other the active substances or substances which is (or are) expected to have a complementary treatment effect.

The dosages at which the carotenoids are administered can vary according to the type of application and the conditions of the subject.

The galenical forms can be doses of powder in sachets, or they can take the form of tablets, capsules, pills, lozenges or gelatin capsules. The drug according to the invention can also be administered in liquid form, that is to say solutions, suspensions or oily or aqueous emulsions.

The unit dose is, for example, between 0.1 and 50 mg.

As mentioned above, there is no upper limit for the administration; nevertheless, it will be fitting to adopt a unit dose which avoids any pigmentation effect of the skin.

Thus, the daily dosage is preferably from 0.3 to 300 mg of carotenoid or carotenoids, and this is achieved, for example, by administering from two to six tablets for gelatin capsules containing from 0.1 to 80% by weight of active principle.

The above indications are given purely for guidance in the context of a treatment using carotenoids alone as active substances. if the carotenoid or carotenoids is (or are) administered in combination with other drugs which are active in treating acne, the doses stated above can be reduced somewhat.

Among the drugs which can be combined with the carotenoids, there may be mentioned active substances of the antibiotic type, such as tetracyclines.

To enable the subject of the present invention to be better understood, there will now be described, by way of purely illustrative and non-limitative examples thereof, several formulations of drug compositions according to the invention.

EXAMPLE 1

A gelatin capsule having the following composition is prepared:

| | |
|---|---|
| Canthaxanthin in coated form containing 10% by weight of active substance | 15.0 mg |
| Polyoxyethylene glycol (molecular weight 6,000) | 9.5 mg |
| Microcrystalline cellulose q.s. | on gelatin capsule filled with about 260 mg |

The shell of the capsule consists of the combination: gelatin/iron oxide/titanium oxide.

One gelatin capsule having the composition defined above is administered regularly, night and morning for 15 days, to an acne patient who has just undergone a 1-month anti-acne treatment with benzoyl peroxide, some of the patient's comedos not having completely disappeared. A gradual decline in the development and number of these comedos is observed.

In the saame manner, another acne patient was treated who had, likewise, just undergone a 2-month anti-acne treatment with benzoyl peroxide, following which treatment the comedos had completely disappeared. It was possible to observe an improvement in the general appearance of his skin without reappearance of comedos.

EXAMPLE 2

A gelatin capsule having the following composition is prepared:

| | |
|---|---|
| Canthaxanthin in coated form containing 10% by weight of active substance | 15.0 mg |
| Tetracycline | 20.0 mg |
| Polyoxyethylene glycol (molecular weight 6,000) | 9.5 mg |
| Microcrystalline cellulose q.s. | one capsule filled with about 260 mg |

The shell of the gelatin capsule consists of the combination defined in Example 1.

One gelatin capsule having the composition defined above is administered regularly, night and morning for 15 days, to a patient whose skin shows acne. A substantial decline in the development and number of comedos is observed.

EXAMPLE 3

Granules are prepared having the following composition:

| | |
|---|---|
| δ-carotene | 18 mg |
| Mixture of granules of sucrose and starch | 200 mg |

A tablespoonful of granules is administered three times daily for a period of one month to an acne patient. A decline is observed in the number of comedos.

We claim:

1. A composition for treating or preventing acne by oral administration comprising an orally administrable pharmaceutically acceptable carrier and a carotenoid selected from the group consisting of α-carotene, δ-carotene, γ-carotene, β-carotene-4,4'-dione, ethyl 8'-apo-β-caroten-8'-oate, β-apo-8'-carotenal, ψ,ψ-carotene, ψ,ψ-carotene-16,16'-diol and ψ,ψ-caroten-16-ol, said carotenoid being present in an amount ranging from 0.001 to 10 percent by weight based on the total weight of said composition and at least one further substance, other than said carotenoid, effective in the treatment of acne, said further substance being present in an amount ranging from 0.001 to 15 percent by weight based on the total weight of said composition.

2. The composition of claim 1 wherein said further substance is an antibiotic.

3. The composition of claim 1 which also contains at least one antioxidant present in an amount ranging from 0.001 to 2 percent by weight based on the total weight of said composition.

4. The composition of claim 3 wherein said antioxidant is vitamin E, t.-butyl hydroquinone, butylated hydroxyanisole or butylated hydroxy toluene.

5. A method for treating acne comprising orally administering to a person suffering from acne an effective amount of a composition comprising an orally administrable pharmaceutically acceptable carrier and a carotenoid selected from the group consisting of α-carotene, δ-carotene, γ-carotene, β-carotene-4,4'-dione, ethyl 8'-apo-β-caroten-8'-oate, β-apo-8'-carotenal, ψ,ψ-carotene, ψ,ψ-carotene-16,16'-diol and ψ,ψ-caroten-16-ol, said carotenoid being present in an amount ranging from 0.001 to 10 percent by weight based on the total weight of said composition.

6. The method of claim 5 wherein said composition also includes at least one further substance, other than said carotenoid, effective in the treatment of acne, said further substance being present in an amount ranging from 0.001 to 15 percent by weight based on the total weight of said composition.

* * * * *